United States Patent [19]

Holick et al.

[11] 4,335,120

[45] Jun. 15, 1982

[54] ADMINISTRATION OF BIOLOGICALLY ACTIVE VITAMIN $D_3$ AND VITAMIN $D_2$ MATERIALS

[75] Inventors: Michael F. Holick, Sudbury, Mass.; Milan R. Uskokovic, Upper Montclair, N.J.

[73] Assignee: Hoffmann-La Roche Inc., Nutley, N.J.

[21] Appl. No.: 203,291

[22] Filed: Nov. 3, 1980

Related U.S. Application Data

[60] Continuation-in-part of Ser. No. 137,673, Apr. 4, 1980, abandoned, which is a division of Ser. No. 22,393, Mar. 21, 1979, Pat. No. 4,230,701.

[51] Int. Cl.$^3$ .................. A61K 31/59; A61K 31/56
[52] U.S. Cl. ........................ 424/236; 424/238
[58] Field of Search ................. 424/236, 238

[56] References Cited

U.S. PATENT DOCUMENTS

| | | | |
|---|---|---|---|
| 2,060,228 | 11/1936 | Lorenz | 424/236 |
| 3,981,996 | 9/1976 | Leigh | 424/243 |
| 4,022,891 | 5/1977 | Takeshita et al. | 424/236 |

FOREIGN PATENT DOCUMENTS 102939  7/1931  Hungary .................. 424/236

OTHER PUBLICATIONS

Amer. Perf. & Essen. Oil Review, (1) (1953) pp. 19, 21–24.
Amer. Perf. & Essen. Oil Review, (Feb. 1953) pp. 117–121 Wells.
Chem. Abst. 85, 83131(x) (1976)—Kanebo Ltd.
Chem. & Physio. of Vit.—Rosenberg—1945—pp. 419–426 Inters. Publ. Inc. N.Y., N.Y.

*Primary Examiner*—Douglas W. Robinson
*Attorney, Agent, or Firm*—Jon S. Saxe; George M. Gould; William H. Epstein

[57] ABSTRACT

A process for administering biologically active vitamin $D_3$ and vitamin $D_2$ materials into the blood system of a subject by providing the biologically active vitamin $D_3$ or $D_2$ material to the skin whereby the skin releases the biologically active vitamin $D_3$ or $D_2$ material into the blood system in a controlled and prolonged manner.

27 Claims, 4 Drawing Figures

ADMINISTRATION OF BIOLOGICALLY ACTIVE VITAMIN $D_3$ AND VITAMIN $D_2$ MATERIALS

CROSS REFERENCE TO RELATED APPLICATIONS

This application is a continuation-in-part application of U.S. application Ser. No. 137,673, filed Apr. 4, 1980, now abandoned, which in turn is a divisional application of Ser. No. 22,393, filed Mar. 21, 1979, now U.S. Pat. No. 4,230,701 issued Oct. 28, 1980.

BACKGROUND OF THE INVENTION

Biologically active vitamin $D_3$ and vitamin $D_2$ materials, due to their action in increasing serum calcium have been utilized in the treatment of various calcium metabolic disorders. Among these disorders include chronic renal disease, Vitamin D resistant rickets, glucocorticord-induced decrease in calcium absorption, osteoporosis, senile decrease in calcium absorption, hypoparathyroidism, turkey weak leg diseases, milk fever diseases, and the like. In the past, biologically active Vitamin $D_3$ and Vitamin $D_2$ materials have been administered to patients orally or intravenously.

A danger in administering biologically active viatmin $D_3$ and vitamin $D_2$ materials orally or intravenously to patients is that the therapeutic to toxic ratio (therapeutic index) of this drug is low and an exess of the drug in the blood stream, especially after administration, can cause episodes of hypercalcemia and hypercalcuria. While hypercalcemia and hypercalcuria can be corrected to a large degree by decreasing the dose of the drug, there is always the danger of hypercalcemia and hypercalcuria repeatedly occuring each time a patient receives a given oral or intravenous dose. This is believed due to the fact that immediately after administration of these drugs, the drug is transported in high concentrations across the small intestine which is one of the principal sites of activity for these drugs. Thus, especially after oral administration, the small intestine is initially exposed to very high concentrations of these metabolites which in turn could induce a very rapid uncontrolled rise in intestinal calcium transport which is reflected in high serum calcium levels in the blood.

Therefore, it has been desired to provide a means for administering biologically active vitamin $D_3$ or vitamin $D_2$ materials to avoid the uncontrolled increase in serum calcium levels which could occur immediately after administration of the biologically active vitamin $D_3$ and vitamin $D_2$ materials.

SUMMARY OF INVENTION

In accordance with this invention, it has been found that when biologically active vitamin $D_3$ and vitamin $D_2$ materials are administered for therapeutic purposes on or into the skin of a subject, the skin acts as a transport medium for the biologically active vitamin $D_3$ and vitamin $D_2$ materials. By acting as a transport mechanism whereby these materials are allowed to enter the blood stream of the circulatory system of the subject, these biologically active vitamin $D_3$ or vitamin $D_2$ materials are transported into the blood stream in a slow and controlled manner. Through this mechanism, the biologically active vitamin $D_3$ and vitamin $D_2$ materials are administered to patients without a rapid and uncontrolled rise in the serum calcium levels which occur during administration by oral and injection means.

Furthermore, when these biologically active vitamin $D_3$ and vitamin $D_2$ materials are provided to the skin of subjects through application on or into the skin, the rise in the intestinal calcium response and in the serum calcium levels induced by a single application can last for at least two weeks after application while a single oral dose of the same quantity is substantially effective for about seven days. Hence, by the procedure of this invention, the need for several repeated doses of the biologically active vitamin $D_3$ and vitamin $D_2$ materials for controlling calcium levels in a given period is substantially reduced thereby reducing the danger of the uncontrolled and rapid rise of serum calcium level which would occur after each administration of the dose to cause hypercalcemia and hypercalcuria.

The process of this invention is carried out by providing to the skin of the subject to be treated a biologically active vitamin $D_3$ or $D_2$ material and allowing this biologically active material to transport through the skin into the blood stream. In carrying out the process of this invention, any conventional method of providing a biologically active vitamin $D_3$ or vitamin $D_2$ material to the skin can be utilized. Once the biologically active vitamin $D_3$ or vitamin $D_2$ materials are applied to the skin, the skin will act as a means for storing and transporting the biologically active materials into the circulation system of the subject. The skin acts as a vehicle for transport of the biologically active materials to the blood system in such a manner that it is only released onto the blood system in such a controlled manner that the rise in the serum calcium level is regulated thereby preventing a rapid uncontrolled rise. Furthermore, the skin acts as a means for storing the biologically active vitamin $D_3$ or vitamin $D_2$ active material so that one administration of the biologically active vitamin $D_3$ or vitamin $D_2$ materials to the skin can regulate the serum calcium level for at least two weeks.

DETAILED DESCRIPTION

In accordance with this invention, any conventional method of providing a biologically active vitamin $D_2$ or $D_3$ material to the skin of a subject can be utilized. Among the conventional methods is by applying to the skin the biologically active vitamin $D_2$ or $D_3$ material are included applying this material topically intraepidermally, intradermally or into the subcutaneous fat.

The vitamin $D_2$ or $D_3$ material can, in accordance with one embodiment of this invention, be applied to the skin topically. In accordance with this embodiment, the biologically active vitamin $D_2$ or $D_3$ material can be applied to the skin either as the biologically active vitamin $D_2$ or $D_3$ material itself or as the corresponding previtamin or corresponding provitamin. Any conventional method of topical application or conventional topical preparation can be utilized to apply either the provitamin or previtamin of the biologically active vitamin $D_3$ or $D_2$ material or even the biologically active $D_2$ or $D_3$ material itself to the skin. In the case where the biologically active vitamin $D_3$ or vitamin $D_2$ material is provided to the skin by the provitamin of the biologically active vitamin $D_2$ or $D_3$ materials, the provitamin is applied topically to the skin and the skin is subjected to ultra-violet light radiation. The ultra-violet radiation converts the provitamin to the corresponding previtamin of the biologically active vitamin $D_2$ or vitamin $D_3$ material. This previtamin is a relatively unstable material which upon exposure at room temperature to the skin isomerizes to the biologically active vitamin $D_2$ or $D_3$ material. Therefore, the biologically active vitamin $D_2$ or vitamin $D_3$ material can be provided to the skin by either the provitamin or previtamin $D_3$ corresponding to the biologically active vitamin $D_2$ or vitamin $D_3$ material. The previtamin corresponding to the biologically active vitamin $D_2$ or $D_3$ material can be topically or intradermally applied to the skin and allowed to isomerize on the skin to the biologically active vitamin $D_2$ or $D_3$ material. On the other hand, the biologically vitamin $D_2$ and vitamin $D_3$ active material itself can be topically applied to the skin thereby causing the skin to act as a transport medium for releasing the vitamin $D_2$ or $D_3$ active material to the blood system.

Where the biologically active vitamin $D_2$ and $D_3$ material is applied to the skin intradermally, intraepidermally or into the subcutaneous fat tissue, it is generally preferred to apply the biologically active vitamin $D_2$ or $D_3$ material and its corresponding previtamin. On the other hand, application of provitamins by these methods to provide the corresponding previtamin to the skin may require a high degree of ultraviolet light radiation, depending upon the pigmentation of the skin, to convert the provitamin to corresponding biologically active vitamin $D_2$ or $D_3$ material. Therefore, it is generally not preferable to apply the vitamin $D_2$ or $D_3$ material to the skin, by introducing the corresponding provitamin intradermally, intraepidermally or into the subcutaneous fat tissue.

The improved results of this invention are achieved through administering the biologically active vitamin $D_2$ and $D_3$ materials to the skin of various subjects such as mammals as well as avian species such as turkeys, chickens, etc. The method of this invention, is useful in treating conditions characterized by low serum levels of vitamin $D_2$ or $D_3$, especially where these levels result from an inability or an impared ability to convert vitamin $D_2$ or vitamin $D_3$ to its biologically active metabolite. These conditions include among others, chronic renal disease, vitamin D resistant rickets, glucocorticord-induced decrease in calcium absorption, osteoporosis, senile decrease in calcium absorption, hypoparathyroidism, milk fever disease, turkey weak leg disease, etc.

By administering the biologically active vitamin $D_2$ or vitamin $D_3$ materials to subjects whose ability to convert vitamin $D_2$ or vitamin $D_3$ to these biologically active forms is impaired, one is able to provide the necessary biologically active forms of these vitamins to subjects. Therefore, any biologically active form of vitamin $D_2$ or $D_3$ can be administered in accordance with this invention. Among the preferred active forms of vitamin $D_2$ and vitamin $D_3$ which can be administered in accordance with this invention are the biologically active metabolites of vitamin $D_2$ and vitamin $D_3$ as well as analogues thereof. These biologically active metabolites and analogues contain the vitamin $D_2$ and $D_3$ structures and have at least one hydroxy group in addition to the hydroxy group present in the vitamin $D_2$ or vitamin $D_3$ structure and may also contain a halo substituent. Among the biologically active vitamin $D_2$ or $D_3$ material compounds of the formula are preferred:

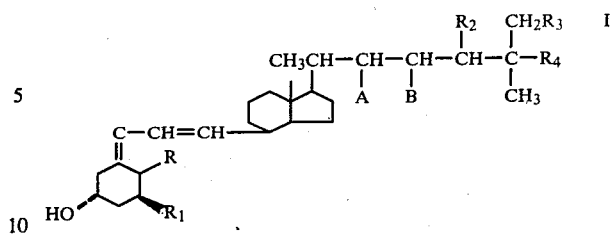

wherein R is methylidene or methyl; $R_2$ is hydrogen hydroxy or methyl; $R_1$, $R_3$ and $R_4$ are hydrogen, hydroxy or halogen; A and B are individually hydrogen or take together form a carbon to carbon bond; with the proviso that at least one of $R_1$, $R_2$, $R_3$ or $R_4$ is hydroxy and with the further proviso that when A and B form a carbon to carbon bond, $R_2$ is methyl.

The previtamins corresponding to the biologically active vitamin materials of formula I have the formula:

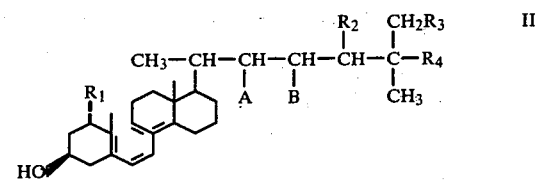

wherein $R_1$, $R_2$, $R_3$, $R_4$ and A and B are as above with the proviso that at least one of $R_1$, $R_2$, $R_3$ or $R_4$ is hydroxy and with the further proviso that when A and B form a carbon to carbon bond, $R_2$ is methyl.

The provitamins corresponding to the biologically active materials have the formula:

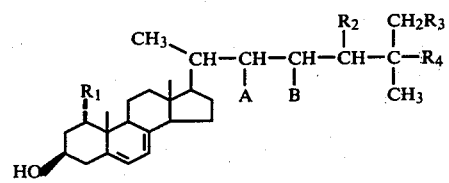

where $R_1$, $R_2$, $R_3$, $R_4$ and A and B are as above with the proviso that at least one of $R_1$, $R_2$, $R_3$ or $R_4$ is hydroxy; and with the further proviso that when A and B form a carbon to carbon bond, $R_2$ is methyl.

In all of the formulae given above, one or more of the hydroxy groups can be esterified with a lower alkanoyl group containing from 2 to 7 carbon atoms such as acetyl.

Among the preferred biological active vitamin $D_2$ and $D_3$ materials which are applied in accordance with this invention are the biological active metabolites and analogues of vitamin $D_2$ and vitamin $D_3$ as well as the corresponding provitamins and previtamins of these biologically active vitamin $D_2$ or $D_3$ metabolites or analogues.

Among the preferred provitamins of these biologically active vitamin $D_2$ or $D_3$ metabolites or analogues are included:

1α,25-dihydroxy-7-dehydrocholesterol[1α,25-(OH)$_2$-proD$_3$];

1α,24,25-trihydroxy-7-dehydrocholesterol[1α,24,25-(OH)$_3$proD$_3$];

24,25-dihydroxy-7-dehydrocholesterol[24,25-(OH)$_2$-proD$_3$];
1α-hydroxy-7-dehydrocholesterol[1α-OHproD$_3$];
1α,24-dihydroxy-35-fluoro-7-dehydrocholesterol[-1α,24-(OH)$_2$25FproD$_3$];
25,26-dihydroxy-7-dehydrocholesterol[25,26-(OH)$_2$-proD$_3$];
25-hydroxy-7-dehydrocholesterol[25-(OH)proD$_3$];
1α-hydroxy-ergosterol[1α-OHproD$_2$];
25-hydroxy-ergosterol[25-OHproD$_2$]; and
1α,25-dihydroxy-ergosterol[1α,25-(OH)$_2$proD$_2$].

Among the preferred previtamin D$_3$ metabolites are:
1α,25-dihydroxy-precholecalciferol[1α,25-(OH)$_2$-preD$_3$];
1α,24,25-trihydroxy-precholecalciferol[1α,24,25-(OH)$_3$preD$_3$];
24,25-dihydroxy-precholecalciferol[24,25-(OH)$_2$-preD$_3$];
1α-hydroxy-percholecalciferol[1α-OHpreD$_3$];
1α,24-dihydroxy-25-fluoro-precholecalciferol [1α,24-(OH)$_2$25FpreD$_3$]; and
25-hydroxy-precholecalciferol [25-OHpreD$_3$].
1α-hydroxy-previtamin D$_2$[1α-OHpreD$_2$];
25-hydroxy-previtamin D$_2$[25-OHpreD$_2$] and
1α,25-dihydroxy-previtamin D$_2$[1α,25-(OH)$_2$preD$_2$].

The following biologically active vitamin D$_2$ and D$_3$ compounds are particularly preferred:
Dihydrotachysterol$_2$;
Dihydrotachysterol$_3$;
5,6-trans-vitamin D$_3$;
25-hydroxy-5,6-trans vitamin D$_3$;
1α-hydroxy vitamin D$_2$[1α-OHD$_2$];
25-hydroxy vitamin D$_2$[25-OHD$_2$];
1α,25-dihydroxy vitamin D$_2$[1α,25-(OH)$_2$D$_2$].
1α,25-dihydroxy-cholecalciferol[1α,25-(OH)$_2$D$_3$];
1α,24,25-trihydroxy-cholecalciferol[1α,24,25-(OH)$_3$D$_3$];
24,25-dihydroxy-cholecalciferol[24,25-(OH)$_2$D$_3$];
1α,24-dihydroxy-25-fluoro-cholecalciferol[1α,24-(OH)$_2$25FD$_3$];
25-hydroxy-cholecalciferol[25-OHD$_3$]; and
1α-hydroxy-cholecalciferol[1α-OHD$_3$]

Among these preferred vitamin D$_3$ compounds, the vitamin D$_3$ compound where the 24-hydroxy group has the R configuration is especially preferred. Also preferred are those 24,25-dihydroxy-vitamin D$_3$ compounds where the 24-hydroxy group has an R-configuration.

The aforementioned biologically active vitamin D$_2$ and D$_3$ materials, their corresponding previtamins and provitamins can be applied to the skin topically or intradermally, intraepidermally or subcutaneous utilizing any conventional method for applying pharmaceuticals in this manner. In general, one application can contain at least 0.05 micrograms of the active material per administration. Generally, these materials can be applied in amounts of 0.5 to about 100 micrograms per administration with 0.1 to 10 micrograms per administration being preferred. In general, amounts of these biologically active vitamin D$_2$ or D$_3$ materials, i.e. either as the previtamin, vitamon or provitamin can be applied typically in doses of greater than 100 micrograms per administration. This is especially true since through the application of these materials to the skin, the amount of the biologically active vitamin D$_3$ or D$_2$ materials transported to the bloodstream is regulated and stored in the skin. Therefore, the danger of applying the biologically active vitamin D$_3$ or D$_2$ materials in excessive dosages is minimized through the controlled transport by the skin to the bloodstream.

When provitamin D$_3$ corresponding to the biologically active vitamin D$_2$ or D$_3$ material is applied to the skin, the provitamin is converted to the corresponding previtamin by the exposure to ultraviolet light. This ultraviolet light can be the sun or can be supplied through a conventional ultraviolet light lamp. Generally when a ultraviolet light lamp is utilized and the provitamin supplied topically to the skin, 0.1 to 10 joules per square centimeter per second is applied. The light can be applied for a fraction of a second to ten hours or longer. The amount of light supplied is not critical. The previtamin which is formed on the skin is isomerized to the biologically active vitamin D$_2$ or D$_3$ material by exposure to the skin at room temperature. The skin provides the means for thermally isomerizing the previtamin to the biologically active vitamin D$_2$ or D$_3$ material.

The biologically active vitamin D$_2$ and D$_3$ materials as well as their previtamins and provitamins, can be applied to the skin through conventional methods. Any conventional topical subcutaneous or intradermal preparation can be utilized to apply these materials to the skin. Any of the means conventional in applying pharmaceuticals in topical subcutaneous or intradermal forms with conventional pharmaceutical carriers can be utilized in accordance with this invention.

For topical administration, the biologically active vitamin D$_2$ and D$_3$ materials as well as their previtamins and provitamins can be conventionally prepared as ointments, tinctures, creams, gels, solutions, lotions, sprays, suspensions and the like. Ointments, creams and solutions are preferred. The pharmaceutical preparation for topical administration can be prepared by mixing the aforementioned active ingredients with non-toxic, therapeutically inert, solid, or liquid carriers which are customarily utilized in such preparations. When prepared as solutions, the weight concentration of the active ingredient is about from 0.001% to about 7.0%, preferably from 0.02% to 0.5%. When prepared in the form of ointments and creams, the weight concentration of the aforementioned active ingredients are about from 0.001% to about 7.0%, preferably from 0.05% to about 1%. In preparing compositions containing the previtamin of the biologically active vitamin D$_2$ or D$_3$ material, care must be exercised to keep the material under conditions of temperature, i.e. below room temperature to impede its conversion to the biologically active vitamin D$_2$ or D$_3$ material. Furthermore, the previtamin should be applied almost after preparation in view of its instability.

It is contemplated to incorporate into the topical preparations described above additives such as preservatives, thickeners, perfumes and the like which are recognized as being conventional in the art of pharmaceutical compounding. In addition, it is contemplated to incorporate into the topical preparations herein described one or a mixture of conventional antioxidants such as, for example, N-methyl-α-tocopherolamine, tocopherols, butylated hydroxyanisole, butylated hydroxy-toluene, ethoxyquin and the like.

This invention thus also relates to the use of pharmaceutically acceptable cream and ointment compositions of the vitamin $D_2$ or $D_3$ active materials as well as their corresponding pre or provitamins.

Cream base pharmaceutical formulations acceptable for use with vitamin $D_2$ or $D_3$ active materials as well as their corresponding pre or provitamins comprise aqueous emulsions containing a fatty acid alcohol, a semisolid petroleum hydrocarbon, a 1,2-glycol and an emulsifying agent.

Ointment pharmaceutical formulation acceptable for use with vitamin $D_2$ or $D_3$ active materials as well as their corresponding pre or provitamins comprise admixtures of a semi-solid petroleum hydrocarbon with a solvent dispersion of the active material.

Cream composition of the vitamin $D_2$ or $D_3$ active materials as well as their corresponding pre or provitamins, preferably comprise emulsions formed from a water phase of a humectant, a viscosity stabilizer and water, an oil phase of a fatty acid alcohol, a semi-solid petroleum hydrocarbon and an emulsifying agent and a phase containing the active ingredient dispersed in an aqueous stabilizer-buffer solution.

The water phase comprises, as the humectant, a pharmaceutically acceptably polyhydric alcohol as, for example, a 1,2-glycol of the formulat $RCHOHCH_2OH$ wherein R is an alkyl of from 1 to 5 carbon atoms. A particularly effective polyhydric alcohol, and the preferred one of this invention, is propylene glycol. Although the polyhydric alcohols help to maintain active ingredients in the emulsion, their concentration therein is not critical, an effective concentration being from about 5 to about 20% by weight with a preferred concentration being from about 12 to about 15% by weight.

A methyl cellulose or hydroxypropylmethyl cellulose may be added to stabilize the viscosity of the cream during storage. Particularly effective is a hydroxypropylcellulose known as Methocel 65 HG 4000 from Dow Chemical. The effective concentration range is from about 0.1 to about 5% by weight with from about 0.5 to about 0.8% preferred.

In the oil phase, the fatty acid alcohol component, which functions as a stabilizer, is derived from the reduction of a long-chain saturated fatty acid of from about 14 to about 20 carbon atoms as, for example, stearyl and cetyl alcohol. The effective concentration is from about 10 to about 30% by weight with an optimum concentration of from about 15 to about 20% by weight. Stearyl alcohol is the preferred component.

The semi-solid petroleum hydrocarbon emollient of the oil phase is a purified mixture of hydrocarbons of the methane series having the formula $CnH2n+2$ and known, in general, by the names petrolatum, petroleum jelly or vaselin. These materials have a melting range of from about 34° to about 54° C., a density range of from about 0.820 to about 0.870 and a refractive index range of from about 1.460 to about 1.474. The preferred material is Petrolatum Perfecta, a purified mixture of semi-solid hydrocarbons ($C_{20}$-$C_{22}$) from petroleum, melting point range 38°-50° C. It is used in concentrations of from about 5 to about 40% by weight with from about 10 to about 15% by weight preferred.

Finally, the oil phase can optionally contain water-soluble emulsifying agents such as polyoxyethylene glycol and polyoxypropylene glycol, used in effective concentrations, i.e., from about 5 to about 8% by weight.

The vitamin $D_2$ or $D_3$ active materials as well as their corresponding pre or provitamins either as prepared or subsequently micronized is sufficiently stable in the excipients used in formulations to provide the concentration needed for therapeutic use.

The invention is illustrated by the following examples. In the examples, Sephadex LH-20 is a hydroxypropyl ether derivative of a polydextran gel. Nedox 1518 Sephadex LH-20 is Sephadex LH-20 modified to contain C15 through C18 aliphatic saturated chains linked by an ether linkage to the polydextran chain of Sephadex LH-20 prepared as disclosed by Ellingboe et al. J. Lipid Res. 11:266-273 (1940). The everted gutsac technique utilized in these examples is described by Martin and DeLuca, Arch. Biochem. Biophys. 134:139-148 (1969). In the Examples, the intestinal calcium transport is given by the ratio of the calcium concentration outside the gutsac (O) to the concentration of calcium inside the inverted gutsac (I) as set forth in the Martin and DeLuca article. The serum calcium determination utilized in the Examples is described by Tanaka et al. Arch. Biochem. Biophys. 146:574-578 (1971).

EXAMPLE 1

Synthesis

[24-tritiated]-1α,25-dihydroxy-7-dehydrocholesterol

Cholesta-24-ene-1α,3β-diacetate (0.1 g) was dissolved in 3 cc tetrahydrofuran (THF) and 2 cc $H_2O$. The mixture was cooled in an ice bath and 70 mg mercuric acetate was added all at once. After 30 min the reaction was removed from the ice bath and the reaction was continued for an additional 24 h at 25° C. The reaction was extracted with diethylether ($Et_2O$) and $H_2O$ and the ether phase was collected and a small portion applied to a silica gel thin layer plate. The plate was developed in 8:2 (v/v) n-hexane/ethylacetate and indicated that greater than 80% of the starting material ($R_f$ 0.7) was converted to the desired mercuryl product, i.e. 1α,3β diacetoxy-25-hydroxy-24 mercuric-cholesterol ($R_f$ 0.3). The product (50 mg) was dissolved in 3 cc THF and 1 cc $H_2O$ and while stirring under $N_2$ 3.36 mg [tritiated]-sodium borohydride S.A. 11.2 Ci/mmole was added. After 30 min at room temperature the reaction was extracted with $Et_2O/H_2O$ the ether phase was collected and the $H_2O$ phase was extracted 2× with $Et_2O$. The $Et_2O$ phases were combined, dried under $N_2$ and dissolved in 1 cc of 19:1 n-hexane/$CHCl_3$ (v:v) and applied to a 1×60 cm glass column containing 15 g of Nedox 1518 Sephadex LH-20 that was slurried, packed and run in the same solvent. Fractions (2 ml) obtained by utilizing the 19:1 n-hexane/$CHCl_3$ (v:v) solvent, were collected and the product containing 24-tritiated 1α,3β-diacetoxy-25-hydroxy-cholesterol was located in fractions 20 through 30. Fractions 20 through 30 were combined dried under $N_2$ and the residue 25 mg was dissolved in 5 cc acetic anhydride containing 0.2 cc pyidine and refluxed. After 24 hr the reaction was dried under $N_2$, redissolved in 0.3 cc 19:1 n-hexane/$CHCl_3$ (v:v) and applied to a 1×60 cm glass column containing Nedox 1518 Sephadex LH-20. The product was collected dried under $N_2$ and the residue (30 mg) of 24-tritiated-1α,3β,25-triacetoxy-cholesterol was dissolved in 5 cc 1:1 n-hexane/benzene (v:v) and warmed to 72° C. in a $H_2O$ bath. 1,3-dibromo-5,5'-dimethylhydantoin (10 mg) was added and after 30 min at 72° C. the reaction was filtered. The filtrate was dried under $N_2$ redissolved in 2 cc xylene and added to a mixture of 0.2 cc trimethylphosphite in 3.0/cc xylene that was maintained at 135° C. After 1.5 hr the reaction was dried under $N_2$ redissolved in 10 cc 19:1 MeOH/$H_2O$ containing 50 mg KOH and refluxed for 24 hr. The reaction was extracted with $CHCl_3$/$H_2O$, the $CHCl_3$ phase collected while the $H_2O$ phase was extracted x2 with $CHCl_3$. The $CHCl_3$ phases were combined dried under $N_2$ redissolved in 1 cc 35:65 n-hexane/$CHCl_3$ (v/v) and applied to a 1×60 cm glass column containing 15 g Sephadex LH-20 that was slurried and packed in the same solvent. Fractions (3 ml) were obtained by eluting the column with 35:65 n-hexane/$CHCl_3$ (v:v) and collected. The compound 24-tritiated-1α,25-dihydroxy-7-dehydrocholesterol was obtained in fractions 90 through 120. This compound was identified by UV adsorption spectra and its ability to co-elute with an authentic sample.

EXAMPLE 2

Topical application of
[24-Tritiated]-1α,25-(OH)$_2$-7-dehydrocholesterol on rats Groups of weanling rats that were maintained on a normal calcium and normal phosphorus vitamin D-deficient diet for 3 wks had their backs shaved. 24 h later 1–2μ Ci [24-tritiated]-1α,25-(OH)$_2$-7-dehydro-cholesterol in 0.1 ml of Wesson oil was topically applied over a 9 cm$^2$ shaved area and 2 h later groups of animals were either left in the dark or exposed to ultraviolet irradiation under a sun lamp (spectral range 253–400 nm) for a total dose of 0.23 joules/cm$^2$ at $\lambda_{max}$297 nm. Immediately after irradiation the animals in both groups were exsanguinated and their skins were removed and frozen on dry ice. The skins were minced and homogenized for 30 sec. The homogenates were extracted with $CHCl_3$:MeOH and the $CHCl_3$ phase was collected, dried under $N_2$ at 0° C. and applied to a 1×60 cm Sephadex LH-20 column packed in and developed with 65:35 $CHCl_3$/n-hexane (v/v). Chromatograms of the lipid extracts from rat skins, small intestines and from the blood of the animals that either remained in the dark or received 0.23 joules/cm$^2$ of ultraviolet irradiation after receiving [24-tritiated] 1α,25-(OH)$_2$-7-dehydrocholesterol were carried out. With respect to the rats which received ultraviolet radiation both 1α,25-(OH)$_2$-7-dehydrocholesterol and 1α,25-(OH)$_2$-cholecalciferol were found in the lipid extracts from the skins, the small intestine and the blood of the rats. On the other hand, only 1α,25-(OH)$_2$-7-dehydrocholesterol and no trace of 1α,25-(OH)$_2$-cholecalciferol was detected in the same lipid extracts from the skins, small intestine and the blood of the rats which were kept in the dark.

EXAMPLE 3

Topical application of
[23,24-tritiated]25-hydroxy-7-dehydrocholesterol on rats

Four rats, which had been on a vitamin D-deficient diet that was adequate in calcium and phosphorus for 2½ weeks, were shaved and 24 hours later were topically dosed over a 9 cm$^2$ area with [23,24-tritiated]-25OH-7-dehydrocholesterol, purified by chromatography just prior to dosing. Each dose contained 8μ Ci in 15 ul 95% ethanol and 40 μl Wesson oil. Two rats, the control group, were kept in the dark. One of these was killed by exsanguination after 2 hours and the other after 24 hours. The other two rats, the treatment group, were placed under a sun lamp (spectral range 253–400 nm) for a total dose of 0.27 joules/cm$^2$. Immediately after irradiation one rat was killed, and the other, 22 hours later. The skin, and small intestine, were removed from each animal and frozen on dry ice.

Individual skins were homogenized in 10 ml 0.9% saline (or in the case of blood, enough 0.9% saline was added to give a total volume of 10 ml) and extracted with 40 ml chloroform; methanol (1:1, v/v). The chloroform phase was collected and the aqueous phase was re-extracted twice with 10 ml chloroform. The chloroform phases were combined, dried under $N_2$ at 4° C., dissolved in n-hexane chloroform (8/2, v/v), and applied to a 1.5×30 cm glass column packed with 15 grams of a Nedox-1518 Sephadex LH-20. The column was eluted with n-hexane:chloroform (8/2, v/v). Fractions (2.0 ml) were collected, dried under air, dissolved in Instagel, and counted for tritium content. With respect to the rats which received ultraviolet light, both 25-hydroxy-7-dehydrocholesterol and 25-hydroxy cholecalciferol were found in major proportions in the lipid extracts of the skins, small intestine and blood of the rats. On the other hand, only 25-hydroxy-7-dehydrocholesterol and no 25-hydroxy-cholecalciferol was found in the same liquid extracts from the skins, small intestines and the blood of the rats which were kept in the dark.

EXAMPLE 4

Topical application of
[24-tritiated]1,25(OH)$_2$-7-dehydrocholesterol on human subjects A group of healthy volunteers of both sexes (age range of 22–30) had 1 cm$^2$ area of buttock exposed to graded doses of ultraviolet irradiation for the purpose of determining their minimal erthyema dose (M.E.D.). After determining each subject's M.E.D., 10μ Ci of [24-tritiated]-1α,25-(OH)$_2$-7-dehydrocholesterol in 5–10 μl of 95% ethanol or Wesson oil was applied to a 1 cm$^2$ area on the buttock and 5 minutes after application this area was either exposed to 3 M.E.D. of ultraviolet irradiation or covered to prevent any light exposure. Immediately after the ultraviolet light exposure, or an equivalent time for the covered subjects, a 6 mm punch biopsy was obtained from the area that received the isotope and immediately frozen on dry ice. Twenty-four hours later 150–200 ml blood was collected.

Each skin sample was extracted with chloroform:methanol:water (2/2/0.8 v/v/v) and the lipid fraction was chromatographed either on a 1.5×30 cm glass column containing 15 g Sephadex LH-20 that was slurried and developed in chloroform:n-hexane (65:35 v/v) or applied directly on a high pressure liquid chromatograph (h.p.l.c.) equipped with a chromatographic column (0.4×30 cm) killed by micro silica acid that was developed with n-hexane:isopropanol (19:1 v/v).

The blood was extracted with chloroform:methanol:blood (2:2:0.8 v/v/v) the chloroform phase was flash evaporated and the lipid residue chromatographed on a 1×60 cm glass column containing 18 g Sephadex LH-20 that was slurried and developed in chloroform:n-hexane (65:35 v/v). Chromatograms of liquid extracts from the punch biopsies of the skin and blood from human subjects were carried out. Both 1α,2-5(OH)$_2$-7-dehydrocholesterol and 1α,25(OH)$_2$ cholecalciferol were found in the liquid extracts from the biopsies of the human skin from the subjects which were exposed to ultraviolet radiation. On the other hand, only 1α,25(OH)$_2$-7-dehydrocholesterol and no 1α25-

(OH)$_2$-cholecaliferol were detected in the lipid fractions obtained from the lipid extracts obtained from the biopsies from human subjects which were not exposed to ultraviolet light.

EXAMPLE 5

1α,25-(OH)$_2$-7-dehydrocholesterol in normal and anephric rats

A group of rats were maintained on a vitamin D-deficient diet for four weeks. After four weeks all of the rats had their backs shaved and 24 h later one-half of each group were bilaterally nephrectomized. Groups of 6 rats received either 10 μg or 50 μg of 1α,25(OH)$_2$-7-dehydrocholesterol dissolved in 0.1 ml Wesson oil applied on their backs over a 1 cm$^2$ area while controls only had the Wesson oil vehicle (0.1 ml) applied to the backs. One hour later they were exposed to a Westinghouse sun lamp (spectral range 253–400 nm) for a total dose of 0.23 joules/cm. Twenty-four hours later the animals were sacrificed their duodena collected for determination of intestinal calcium transport by the everted gut sac technique and their blood was collected for serum calcium determination using a atomic absorption spectrometer.

The results of serum calciums of groups of vitamin D-deficient rats that received a topical dose of 10 μg of 1,25(OH)$_2$-7-dehydrocholesterol and then were either exposed to ultraviolet irradiation or kept in the dark is given in the following table:

TABLE I

| Dose 1,25(OH)$_2$-7-dehydrocholesterol | Nephrectomy | UV | Serum Calcium |
| --- | --- | --- | --- |
| 0 | no | no | 5.6 ± 0.2 |
| 10 μg | no | no | 5.7 ± 0.3 |
| 0 | no | yes | 7.6 ± 0.2 |
| 10 μg | no | yes | 8.4 ± 0.2 |
| 0 | yes | no | 4.6 ± 0.3 |
| 10 μg | yes | no | 4.4 ± 0.4 |
| 10 μg | yes | yes | 5.8 ± 0.2 |

In Table I, the rats were fed a 0.47% calcium, 0.3% phosphorus vitamin D-deficient diet for 4 weeks and then some were bilaterally nephrectomized. There were 6 rats in each group and the values are reported as the mean±SEM.

The results of the efficiency of intestinal calcium transport in vitamin D-deficient anephric rats 24 hours after they had received a topical application of 50 μg of 1,25(OH)$_2$ 7-dehydrocholesterol and then were exposed to ultraviolet irradiation or kept in the dark is given in table 2.

TABLE 2

| Dose of 1α,25(OH)$_2$-7-dehydrocholesterol | UV Exposure | Intestinal Calcium Transport (I/O) |
| --- | --- | --- |
| Control | No | 1.0 ± 0.1 |
| Control | Yes | 1.2 ± 0.1 |
| 50 μg | No | 1.3 ± 0.1 |
| 50 μg | Yes | 3.1 ± 0.3 |

In Table 2, the rats were fed a 0.47% calcium, 0.3% phosphorus vitamin D-deficient diet for 4 weeks and then were bilaterally nephrectomized. There were 6 rats in each group and the values are reported as the mean±SEM.

EXAMPLE 6

By the procedure of Example 6, the following compounds were applied to the skins of rats at dosages of 1 μg dissolved in 20 μl of 95% ethyl alcohol:
1α,25(OH)$_2$D$_3$;
1α(OH)D$_3$; and
1α,24(OH)$_2$25FD$_3$ The control was pure ethyl alcohol.

The results of the intestinal calcium transport response and serum calcium levels from vitamin D-deficient rats that received a topical application of the above compounds, 24 hours previously, is set forth in Table 3.

TABLE 3

| Dose | I/O | Serum Calciums |
| --- | --- | --- |
| Control | 2.3 ± 0.1 | 6.3 ± 0.1 |
| 1α,25(OH)$_2$D$_3$ | 3.8 ± 0.1 | 8.1 ± 0.1 |
| 1αOHD$_3$ | 3.6 ± 0.2 | 8.0 ± 0.2 |
| 1α,24(OH)$_2$25FD$_3$ | 4.2 ± 0.2 | 8.0 ± 0.2 |

EXAMPLE 7

This example demonstrates the prolonged effect of applying either 1α,25(OH)$_2$D$_3$ or 1α,25(OH)$_2$pre D$_3$ topically.

In this experiment, rats were maintained on a Vitamin D-deficient diet adequate in calcium and phosphorus for four weeks. After four weeks, all of the rats had their backs shaved. One group of rats received 1 μg of 1α,25(OH)$_2$pre D$_3$ dissolved in 20 μl of 95% ethyl alcohol and another group of rats received 1 μg of 1α,2-5(OH)$_2$D$_3$ dissolved in 20 μl of 95% ethyl alcohol applied on their backs over a 1 cm$^2$ area while the control group only received 20 μl of 95% ethyl alcohol applied to their backs. Another group of rats had received a dose of 1 μg of 1α,25(OH)$_2$D$_3$ in 20 μl of 95% ethanol orally administered at the same time that this compound was administered topically to the rats. During a period of thirty-five days, a number from each of the group of rats were sacrificed at the same time each day. During this period, the intestinal calcium transport and the serum calcium was measured in the same manner as set forth in Example 6 in each of the sacrificed rats. The results of these tests are given in FIGS. 1 through 4.

In FIG. 1, the results of the control are compared to the results of rats which received either 1α,25(OH)$_2$D$_3$ or 1α,25(OH)$_2$pre D$_3$ topically.

In FIG. 2, the results obtained from the rats which received 1α,25(OH)$_2$D$_3$ and 1α,25(OH)$_2$pre D$_3$ topically are set forth graphically.

In FIG. 3, the results of the control and the results obtained from the rats received 1α,2-5(OH)$_2$D$_3$ orally are compared to the results obtained from rats which received 1α,25(OH)$_2$D$_3$ topically.

In FIG. 4, the results of the control and the results obtained from the rats which received $1\alpha,25(OH)_2D_3$ orally are compared to the results obtained from the rats which received $1\alpha,25(OH)_2D_3$ topically.

Figure 1:
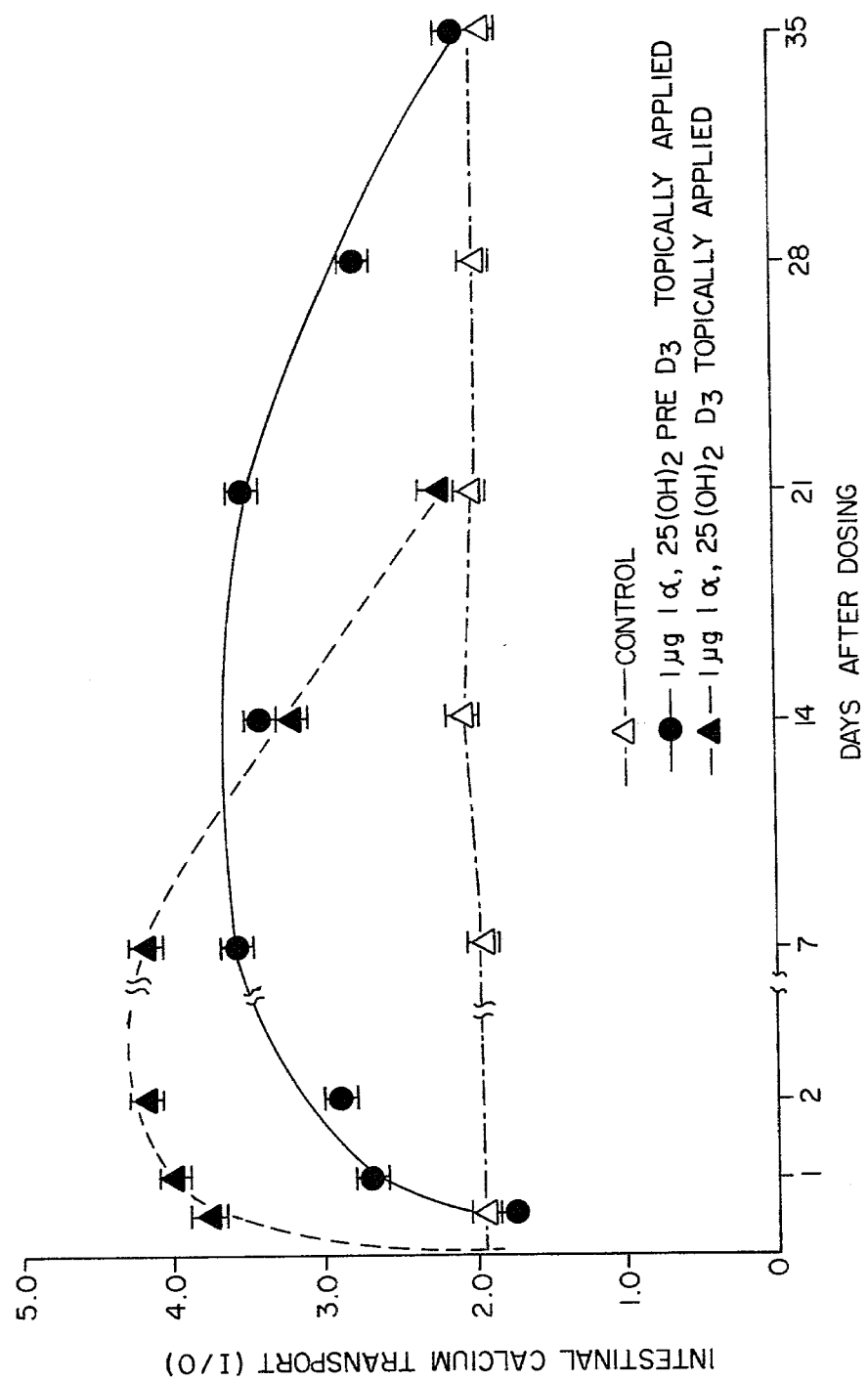
FIG. 1 is a plot of the intestinal calcium transport measured in the sacrificed rats vs. the days after administration of the dose to the rats.
Figure 2:
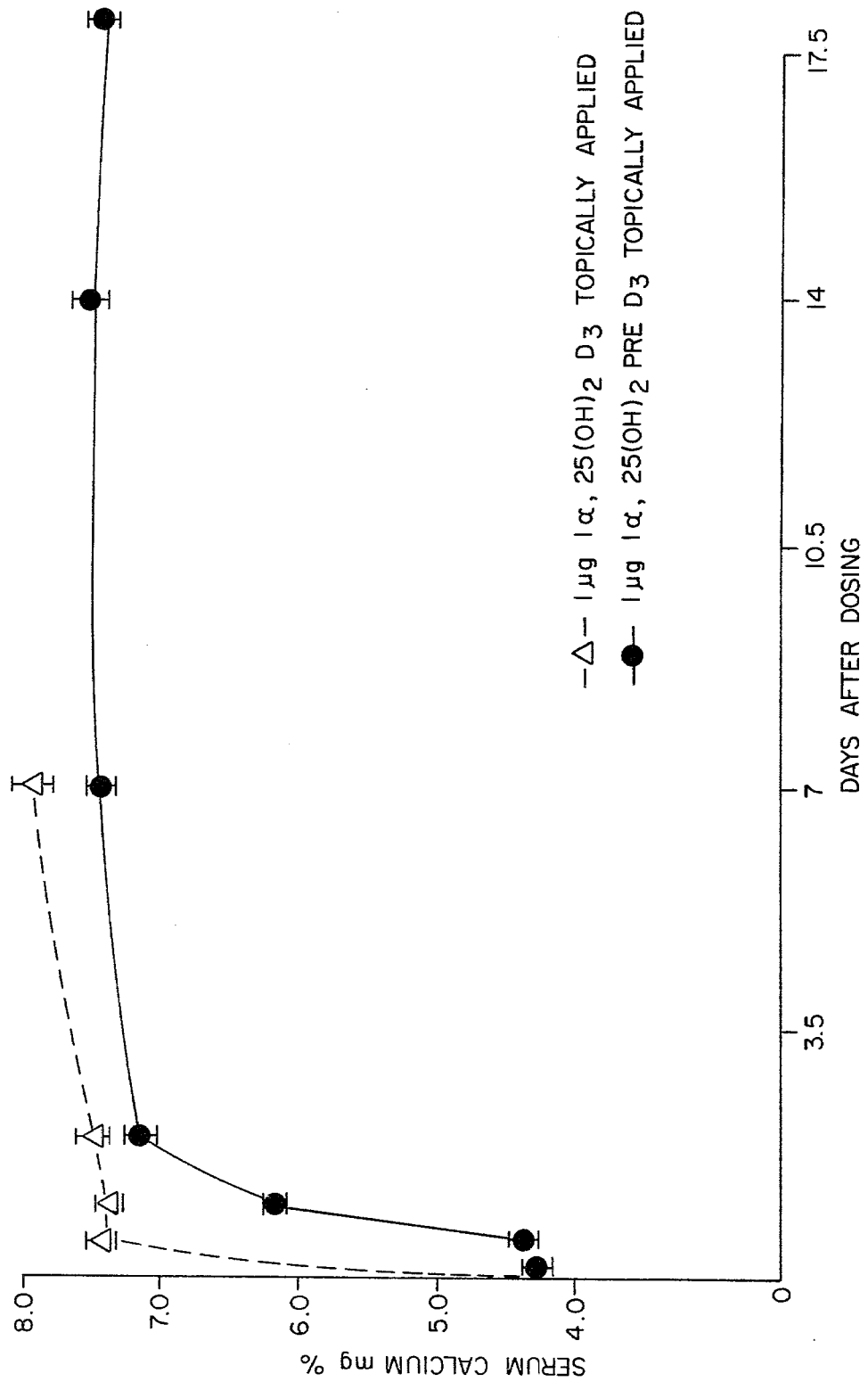
FIG. 2 is a plot of the serum calcium levels measured in the sacrificed rats vs. the days after administration of the dose.

The results in FIGS. 1 and 2 demonstrate that $1\alpha,2$-5$(OH)_2$pre $D_3$ and $1\alpha,25(OH)_2D_3$ when topically applied maintained, for approximately two weeks, an increase in both the intestinal calcium transport response and the serum calcium level in the animals before these levels declined to the control levels by the 21st day.

Figure 3:
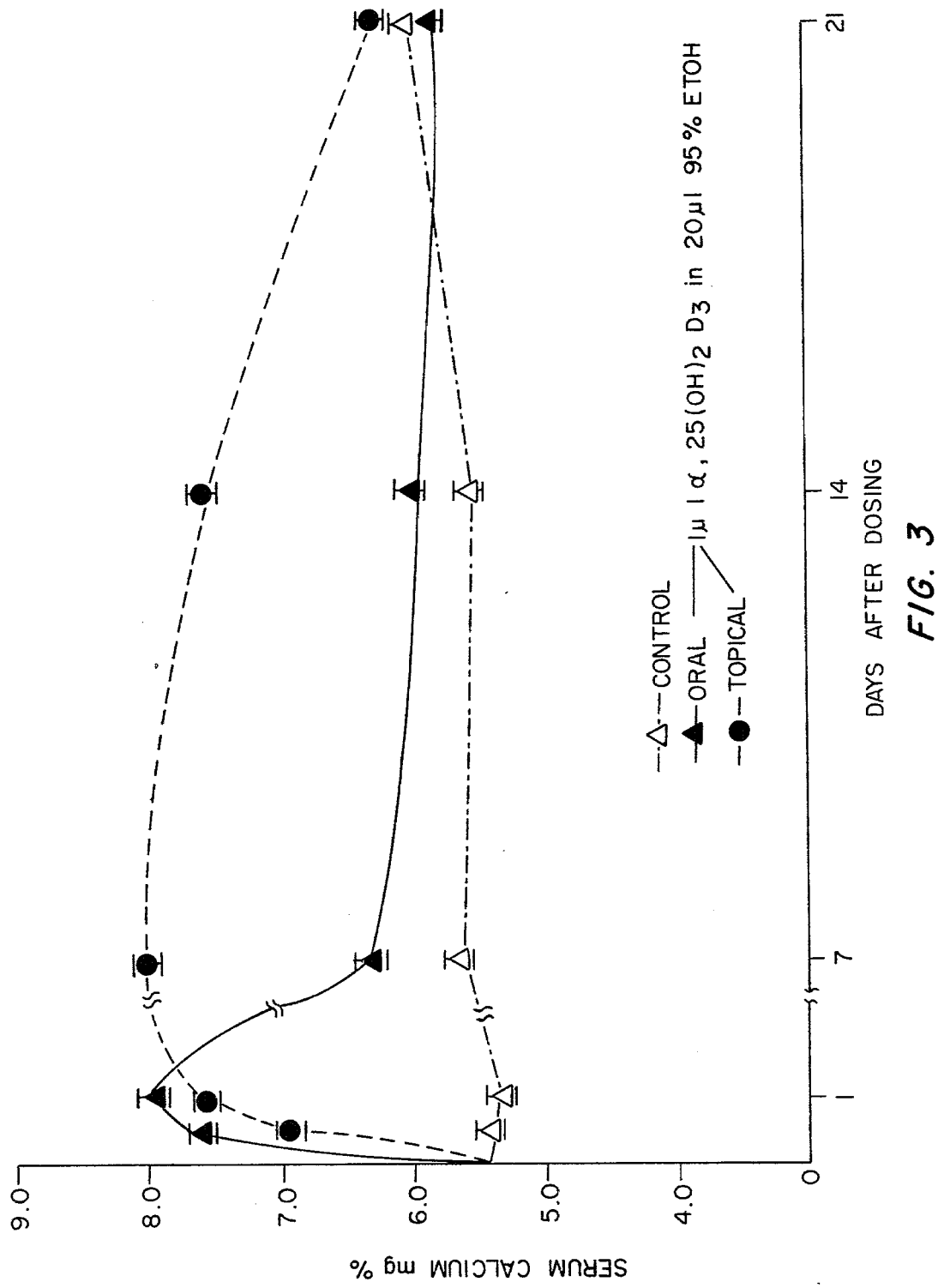
FIG. 3 is a plot of the serum calcium levels measured in the sacrificed rats vs. the days after administration of the dose to the rats.
Figure 4:
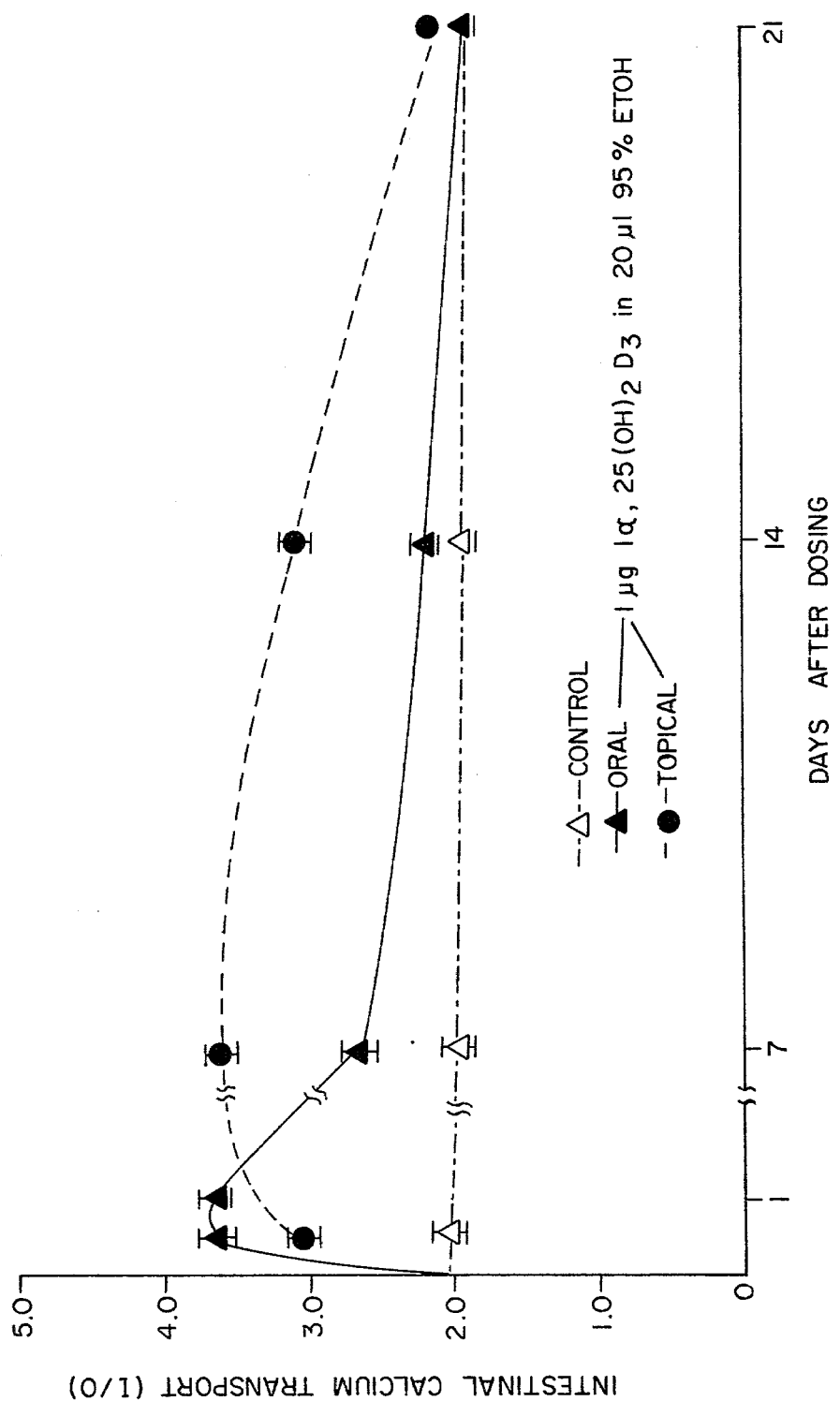
FIG. 4 is a plot of the intestinal calcium transport response measured in the sacrificed rats vs. the days after administration of the dose to the rats.

FIGS. 3 and 4 demonstrate that when $1\alpha,25(OH)_2D_3$ is applied topically to the animals, the serum calcium level and the intestinal calcium transport response were elevated for approximately two weeks after dosing. On the other hand, when $1\alpha,25(OH)_2D_3$ is administered orally, both serum calcium response and intestinal transport level is only substantially elevated for a period of less than 7 days. Furthermore, FIGS. 3 and 4 demonstrate that when $1\alpha,25(OH)_2D_3$ is applied orally, a sharp increase in both serum calcium level and intestinal calcium transport responses occur initially after administration, which sharp increase does not occur when this compound is administered topically.

In examples 8 through 12, the serum $^{45}Ca$ level in the blood stream was measured by orally feeding the chickens 2 microcuries of $^{45}Ca$. Forty-five minutes after feeding $^{45}Ca$ to the chickens, the chickens were sacrificed. The serum $^{45}Ca$ in the blood was measured by the procedure of Haussler et al. *Proc. Natl. Acad.* Sci. USA, volume 70, page 2248 (1973).

EXAMPLE 8

White Leghorn, one-day-old cockerels were placed on a vitamin D-deficient diet and housed under ultraviolet-free lighting. After this period, $1\alpha,25(OH)_2$-previtamin $D_3$ was applied topically to the comb in 0.2 ml 50/50 propylene glycol/ethanol. Eighteen hours later, $^{45}Ca$ absorption was measured. The results are given in the following table:

| Topical Activity of $1\alpha,25(OH)_2$-Previtamin $D_3$ in D-Deficient Chicks | | | |
|---|---|---|---|
| Topical Dose (MCG) | No. of Chicks | Serum $^{45}Ca$ cpm/0.2 ml | |
| 0 | 10 | 1023 ± 69 | |
| 1 | 10 | 1151 ± 172 | |
| 2 | 10 | 1134 ± 87 | |
| 4 | 10 | 1704 ± 101*** | (+66%) |
| 10 | 10 | 2377 ± 131*** | (+132%) |

EXAMPLE 9

White Leghorn one-day-old cockerels were placed on a vitamin D-deficient diet and housed under ultraviolet-free lighting. Twenty-five days later, $1\alpha,2$-5$(OH)_2D_3$ was applied to their combs topically in 0.2 ml propylene glycol/ethanol (50/50, V/V). Eighteen hours later, serum $^{45}Ca$ absorption was measured. The results are given in the following table:

| Topical Activity of $1\alpha,25(OH)_2D_3$ in Vitamin D-Deficient Chicks | | | |
|---|---|---|---|
| Topical Dose (MCG) | No. of Chicks | Serum $^{45}Ca$ cpm/0.2 ml | |
| 0 | 10 | 438 ± 29 | |
| 0.1 | 10 | 558 ± 45* | (+27%) |
| 0.2 | 10 | 698 ± 71** | (+59%) |
| 0.4 | 10 | 882 ± 147** | (+101%) |
| 1 | 10 | 983 ± 119*** | (+124%) |
| 2 | 10 | 1221 ± 105*** | (+179%) |
| 4 | 10 | 1228 ± 54*** | (+180%) |
| 10 | 10 | 1233 ± 74*** | (+182%) |

EXAMPLE 10

The provitamin, $1\alpha,25(OH)_2$-7dehydrocholesterol, dissolved in 50/50 (V/V) propylene glycol/ethanol was applied topically to the combs of chicks which had been fed a vitamin D-deficient diet for three weeks and had been housed under ultraviolet-free lighting. Immediately after application, chicks were exposed to 10 minutes under the Westinghouse FS40 Fluorescent Sun Lamps and were then returned to ultraviolet-free lighting. Eighteen hours later, the serum $^{45}Ca$ was measured. The results are given in the following table:

| Effect on UV Irradiation of D-Deficient Chicks After Topical Application of $1\alpha,25(OH)_2$-7 Dehydrocholesterol on Calcium Absorption | | | | |
|---|---|---|---|---|
| Exp. | Topical Dose (MCG) | No. of Chicks | Serum $^{45}Ca$ cpm/0.2 ml | |
| 1 | 0 | 12 | 877 ± 69 | |
|  | 100 | 12 | 947 ± 104 | |
|  | 200 | 12 | 1120 ± 146 | |
|  | 400 | 12 | 1283 ± 105** | (+46%) |
|  | 1000 | 12 | 1510 ± 123*** | (+72%) |
| 2 | 0 | 17 | 730 ± 64 | |
|  | 150 | 17 | 696 ± 72 | |
|  | 300 | 16 | 1113 ± 125** | (+52%) |
|  | 600 | 14 | 1062 ± 101** | (+45%) |

EXAMPLE 11

Fifty (50) mg of $1\alpha,25(OH)_2$-7 dehydrocholesterol were dissolved in a mixture of 5 ml ethanol and 5 ml propylene glycol. The solution was placed in a quartz tube and suspended horizontally at a distance of one foot under a pair of Westinghouse FS40 Fluorescent Sun Lamps. The irradiated solution (0.2 ml) was applied topically to the combs of chicks which had been fed a vitamin D-deficient diet and housed under ultraviolet-free lighting for 3 weeks. Eighteen hours later, the serum $^{45}Ca$ absorption was measured. The results are given in the following table:

| Effect of Topical Application of UV-Irradiated Solution of $1\alpha,25(OH)_2$-7 Dehydrocholesterol on Calcium Absorption in D-Deficient Chicks | | | |
|---|---|---|---|
| UV (min.) | No. of Chicks | Mean Serum $^{45}Ca$ cpm/0.2 ml | |
| 0 | 7 | 686 | |
| 60 | 7 | 2017*** | (+194%) |
| 0 | 7 | 652 | |
| 5 | 7 | 1259** | (+93%) |
| 15 | 7 | 1570*** | (+141%) |

EXAMPLE 12

An ointment was prepared containing the following ingredients:

| | |
|---|---|
| 1α,25-dihydroxy vitamin D₃ | 2.5% |
| Cholesterol | 3.0% |
| Stearyl Alcohol | 3.0% |
| White Wax | 8.0% |
| White Petrolatum | qs 100 |

Procedure:

Melt all vehicle ingredients in a suitable vessel on a water bath. Discontinue heating and add the 1α,25-dihydroxy vitamin D₃ with stirring and continue stirring until the mixture begins to congeal.

EXAMPLE 13

The ointment of Example 12 was prepared except that it contained 2.5% of 1α,25-dihydroxy provitamin D₃ as the active ingredient.

EXAMPLE 14

An ointment was prepared as in Example 12 except that the active ingredient was 2.5% of 24R,25-dihydroxy provitamin D₃.

EXAMPLE 15

A hydrophilic ointment was prepared as follows:

| | |
|---|---|
| 1α,25-dihydroxy vitamin D₃ | 3% |
| Sodium Lauryl Sulfate | 1% |
| Propylene Glycol | 12% |
| Stearyl Alcohol | 25% |
| White Petrolatum | 25% |
| Methyl Paraben | 0.03% |
| Propyl Paraben | 0.02% |
| Deionized Water | qs 100 |

Procedure:

Melt the stearyl alcohol and petrolatum on a steam bath and warm to about 75° C. Dissolve all other ingredients except the drug in the water and warm to 75° C. Add the aqueous phase to the oil phase with stirring. Powder in the 1α,25-dihydroxy vitamin D₃ to the emulsion and stir until smooth.

EXAMPLE 16

A hydrophilic ointment was prepared as in Example 15 except that 5% of 1α,25-dihydroxy provitamin D₃ was used as the active ingredient.

EXAMPLE 17

A hydrophilic ointment was prepared in accordance with the procedure in Example 15 except that 5% of 24R, 25-dihydroxy provitamin D₃ was the active ingredient.

EXAMPLE 18

A cream was prepared with the following ingredients:

| | |
|---|---|
| Oil Phase | |
| 1α,25-dihydroxy vitamin D₃ | 2.5% |
| Stearic Acid | 14% |
| Cetyl Alcohol | 1% |
| Isopropyl Palmitate | 1% |
| Propyl Paraben | 0.05% |
| Sorbitan Monostearate | 2% |
| Water Phase | |

| | |
|---|---|
| -continued | |
| Methyl Paraben | 0.1% |
| Propylene Glycol | 5% |
| Polysorbate 60 | 1.5% |
| Deionized Water | qs 100 |

Procedure:

Heat the oil phase to 70° C. Add the water phase at 72° C. to the oil phase stirring continuously.

EXAMPLE 19

A cream was prepared in the same manner as Example 18 except that 2.5% of 1 α,25-dihydroxy provitamin D₃ was used as the active ingredient.

EXAMPLE 20

A cream was prepared in the same manner as Example 18 except that 2.5% of 24R, 25-dihydroxy provitamin D₃ was used as the active ingredient.

EXAMPLE 21

A microemulsion gel was prepared with the following ingredients:

| | |
|---|---|
| 1α,25-dihydroxy vitamin D₃ | 0.1% |
| Ethoxylated Lanolin | 25% |
| Glycerine | 10% |
| Isopropyl Myristate | 48% |
| Methyl Paraben | 0.1% |
| Propyl Paraben | 0.025% |
| Deionized Water | qs 100 |

Procedure:

The 1α,25-dihydroxy vitamin D₃, ethoxylated lanolin, isopropyl myristate and propyl paraben are heated to 80° C. The water, glycerine and methyl paraben are heated to 90° C. and added to the oil phase with stirring.

EXAMPLE 22

A microemulsion gel was prepared in the same manner as Example 21 except that 0.1% of 1α,25-dihydroxy provitamin D₃ was used as the active ingredient.

EXAMPLE 23

A microemulsion gel was prepared in the same manner as Example 21 except that 0.1% of 1α,25-dihydroxy provitamin D₃ was used as the active ingredient.

EXAMPLE 24

Weanling male Holtzman rats were maintained on a vitamin D-deficient diet that was adequate in calcium and phosphate for seven weeks. At the end of the seventh week on this diet, each rat had an area (2 cm²) shaved from its back. Two hours later groups of rats (6 rats each) received one of the following modes of administration in 5 to 10 μl of 95% EtOH:
a. 1 μg 1α,25-dihydroxyvitamin D₃ intradermally
b. 1 μg 1α,25-dihydroxyvitamin D₃ subcutaneously
A control group received an intradermal injection of 10 μl 95% EtOH.

The results of the above experimental tests are given in the table below. The intestinal calcium absorption was measured by the everted gut sac technique described by Martin and DeLuca, Arch. Biochem. Biophys. 134:139–148 (1969). In the Table, the intestinal calcium transport is given by the ratio of the concentration of $^{45}Ca$ outside the gut sac (O) to the concentration of $^{45}Ca$ inside the overted gut sec (I) as set forth in the Martin and DeLuca article. The serum calcium determination was determined by the procedure described by Tanaka et al., Arch. Biochem. Biophys. 146:574–578 (1971).

| Dose | Intestinal Calcium Absorption (I/O) | Serum Calcium Level mg/dl |
|---|---|---|
| 10 μl 95% EtOH intradermally (control) | 1.8 ± 0.3 (S.E.M.) | 5.3 ± 0.1 |
| 1 μg 1α,25-dihydroxyvitamin $D_3$ intradermally | 3.4 ± 0.3 | 8.8 ± 0.1 |
| 1 μg 1α,25-dihydroxyvitamin $D_3$ subcutaneously | 3.3 ± 0.3 | 8.7 ± 0.1 |

What is claimed is:

1. A process of administering a therapeutic amount of a biologically active vitamin D material comprising providing to the skin of a subject a therapeutically effective amount of a biologically active vitamin $D_2$ or $D_3$ material of the formula:

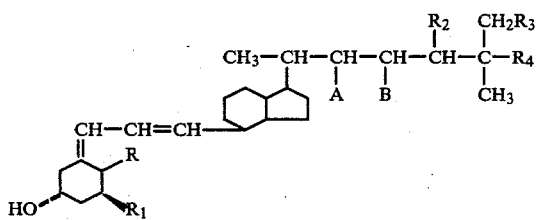

wherein R is methylidene or methyl; $R_2$ is hydrogen, hydroxy or methyl; $R_1$, $R_3$ and $R_4$ are hydrogen, hydroxy or halogen; A and B are individually hydrogen or taken together form a carbon to carbon bond; with the proviso that at least one of $R_1$, $R_2$, $R_3$ or $R_4$ is hydroxy and with the further proviso that when A and B form a carbon to carbon bond, $R_2$ is methyl and allowing the material to transport through the skin into the bloodstream.

2. The process of claim 1 wherein said vitamin D material is provided in situ to the skin by topically applying to said skin a previtamin D material of the formula:

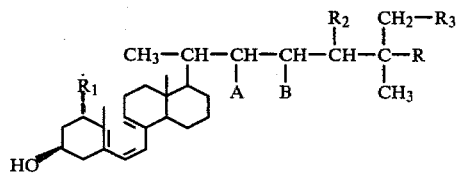

wherein $R_1$, $R_2$, $R_3$, $R_4$ and A and B are as above with the proviso that at least one of $R_1$, $R_2$, $R_3$ or $R_4$ is hydroxy and with the further proviso that when A and B form a carbon to carbon bond, $R_2$ is methyl and thereafter allowing said previtamin D material to be converted to said vitamin D material through contact with said skin.

3. The process of claim 2 wherein said 1α,24,25-trihydroxy vitamin $D_3$ is provided in situ to the skin by topically applying 1α,24,25-trihydroxy provitamin $D_3$ to the skin and thereafter subjecting said skin to ultraviolet light radiation to convert said provitamin to said vitamin.

4. The process of claim 2 wherein said previtamin D material is 24,25-dihydroxy previtamin $D_3$.

5. The process of claim 2 wherein said previtamin D is 1α-hydroxy previtamin $D_3$.

6. The process of claim 2 wherein said previtamin D is 1α,25-dihydroxy previtamin $D_3$.

7. The process of claim 2 wherein said vitamin D active material is provided to the skin by topically applying to the skin a provitamin D material of the formula:

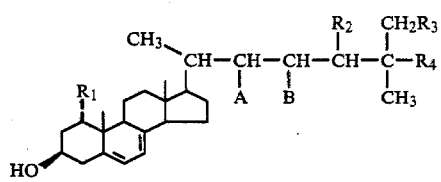

wherein $R_1$, $R_2$, $R_3$, $R_4$ and A and B are as above with the proviso that at least one of $R_1$, $R_2$, $R_3$ or $R_4$ is hydroxy; and with the further proviso that when A and B form a carbon to carbon bond, $R_2$ is methyl and thereafter subjecting said skin to ultraviolet light radiation to convert said provitamin D material to said vitamin D material.

8. The process of claim 7 wherein said provitamin D material is 24,25-dihdyroxy provitamin $D_3$.

9. The process of claim 7 wherein said provitamin is 1α,25-dihydroxy provitamin $D_3$.

10. The process of claim 7 wherein said provitamin is 1α-hydroxy provitamin $D_3$.

11. The process of claim 1 wherein said material is 1α,25-dihydroxy vitamin $D_3$.

12. The process of claim 11 wherein said 1α,25-dihydroxy vitamin $D_3$ is applied topically to the skin.

13. The process of claim 1 wherein said material is 1α-hydroxy vitamin $D_3$.

14. The process of claim 13 wherein said 1α-hydroxy vitamin $D_3$ is applied topically to the skin.

15. The process of claim 1 wherein said material is 1α,24,25-trihydroxy vitamin $D_3$.

16. The process of claim 15 wherein said 1α,24,25-trihydroxy vitamin $D_3$ is applied topically to the skin.

17. The process of claim 15 wherein said 1α,24,25-trihydroxy vitamin $D_3$ is provided in situ to the skin by topically applied 1α,24,25-trihydroxy vitamin $D_3$ to the skin allowing said previtamin to be converted to said vitamin through contact with said skin.

18. The process of claim 1 wherein said material is 24,25-dihydroxy vitamin $D_3$.

19. The process of claim 18 wherein said 24,25-dihydroxy vitamin $D_3$ is applied topically to the skin.

20. The process of claim 1, wherein said material is 25,26-dihydroxy vitamin $D_3$.

21. The process of claim 20 wherein said 25,26-dihydroxy vitamin $D_3$ is applied topically to the skin.

22. The process of claim 20 wherein said 25,26-dihydroxy vitamin $D_3$ is provided in situ to the skin by topically applying 25,26-dihydroxy provitamin $D_3$ to the skin and thereafter subjecting said skin to ultraviolet light radiation to convert said provitamin to said vitamin.

23. The process of claim 22 wherein said 25,26-dihydroxy vitamin $D_3$ is provided in situ to the skin by topically applying 25,26-dihydroxy previtamin $D_3$ to the skin and thereafter allowing said previtamin to be converted to said vitamin through contact with said skin.

24. The process of claim 1 wherein said material is 25-hydroxy vitamin $D_3$.

25. The process of claim 24 wherein said 25-hydroxy vitamin $D_3$ is applied topically to the skin.

26. The process of claim 24 wherein said 25-hydroxy vitamin $D_3$ is provided in situ to the skin by topically applying 25-hydroxy provitamin $D_3$ to the skin and there with subjecting said skin to ultraviolet light radiation to convert said provitamin to said vitamin.

27. The process of claim 24 wherein said 25-hydroxy vitamin $D_3$ is provided in situ to the skin by topically applying 25-hydroxy previtamin $D_3$ to the skin and thereafter allowing said previtamin to be converted to said vitamin $D_3$ through contact with said skin.

* * * * *